(12) United States Patent
Olesen

(10) Patent No.: US 6,265,441 B1
(45) Date of Patent: Jul. 24, 2001

(54) USE OF NO SCAVENGERS, INHIBITORS OF ANTAGONISTS IN THE TREATMENT OF MIGRAINE

(76) Inventor: Jes Olesen, 3 Lemchesvej, DK-2900 Hellerup (DK)

( * ) Notice: Subject to any disclaimer, the term of this patent is extended or adjusted under 35 U.S.C. 154(b) by 0 days.

(21) Appl. No.: 08/737,311

(22) PCT Filed: May 10, 1995

(86) PCT No.: PCT/IB95/00415

§ 371 Date: Nov. 12, 1996

§ 102(e) Date: Nov. 12, 1996

(87) PCT Pub. No.: WO95/31195

PCT Pub. Date: Nov. 23, 1995

(30) Foreign Application Priority Data

May 11, 1994 (EP) .................................................. 94610027

(51) Int. Cl.[7] .................................................. A61K 31/195
(52) U.S. Cl. .................................................. 514/561
(58) Field of Search .................................................. 514/561

(56) References Cited

U.S. PATENT DOCUMENTS 5,807,886 * 9/1998 MacDonald et al. ................ 514/438

FOREIGN PATENT DOCUMENTS

| 0 631 776 | 1/1995 | (EP) . |
| 2 263 111 | 7/1993 | (GB) . |
| 95 05363 | 2/1995 | (WO) . |
| 95 05814 | 3/1995 | (WO) . |

OTHER PUBLICATIONS

Medline Abstract & 7095970 (1986). Balasini et al.*

Medline Abstract 92248872 (1992). Wei et al.*

Olesen, J., et al., *Trends in Pharmacological Science*, May 15, 1994, 149–153.

Wahl, M. et al., *Brain Research*, 637, No. 1–2, Feb. 21, 1994, 204–210.

Olesen, J., et al., *Neuroreport,* 4(8), Aug. 1993, 1027–1030.

Thomsen, L.L., et al., *Cephalalgia, 13*(6), Dec. 1993, 395–399.

* cited by examiner

*Primary Examiner*—Zohreh Fay
(74) *Attorney, Agent, or Firm*—Bacon & Thomas

(57) ABSTRACT

The present invention relates to the use of a NO scavenger or an inhibitor or antagonist in the prophylactic or acute treatment of migraine or other vascular headaches in mammals including humans.

9 Claims, 4 Drawing Sheets

Figure 1:
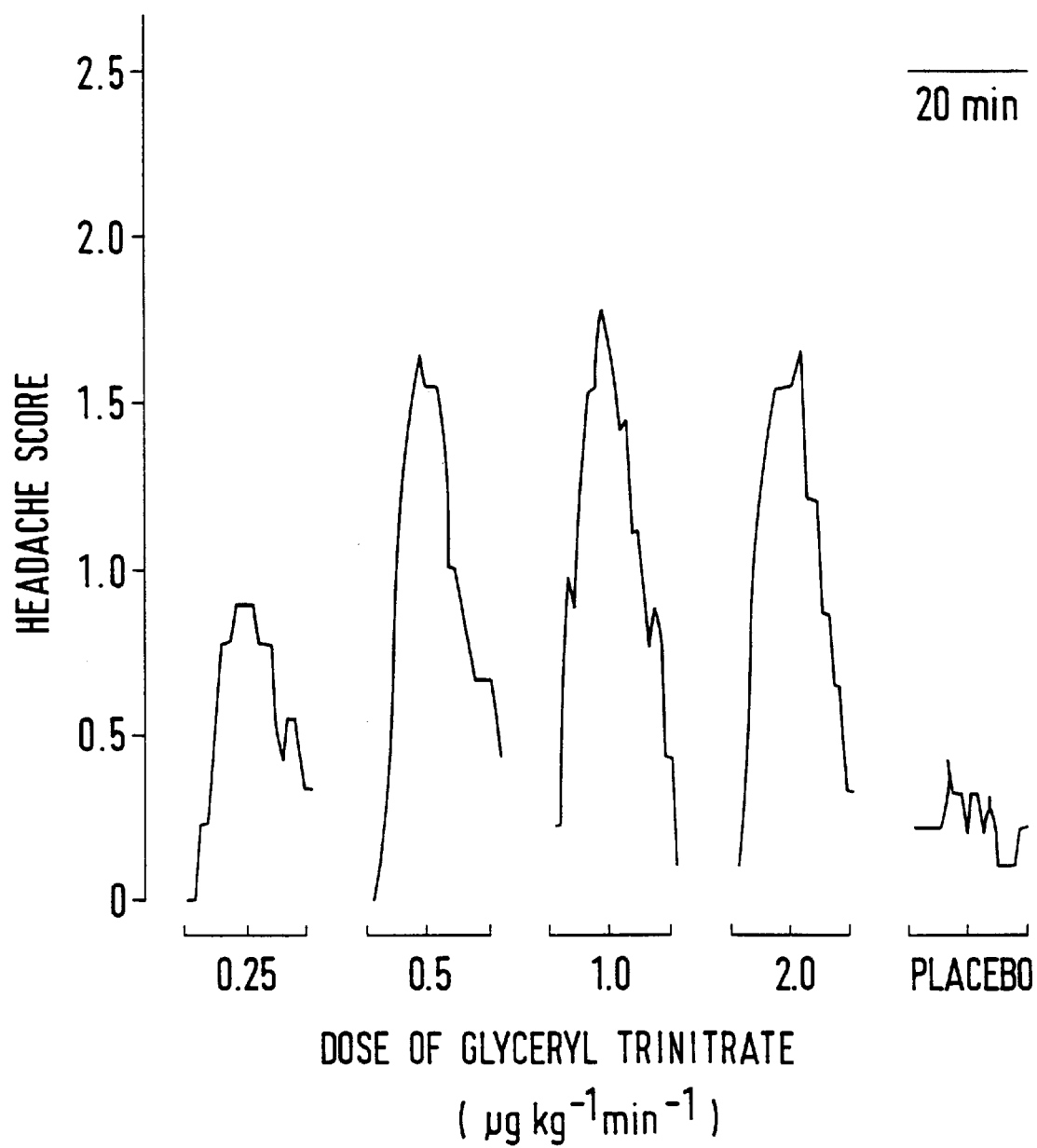

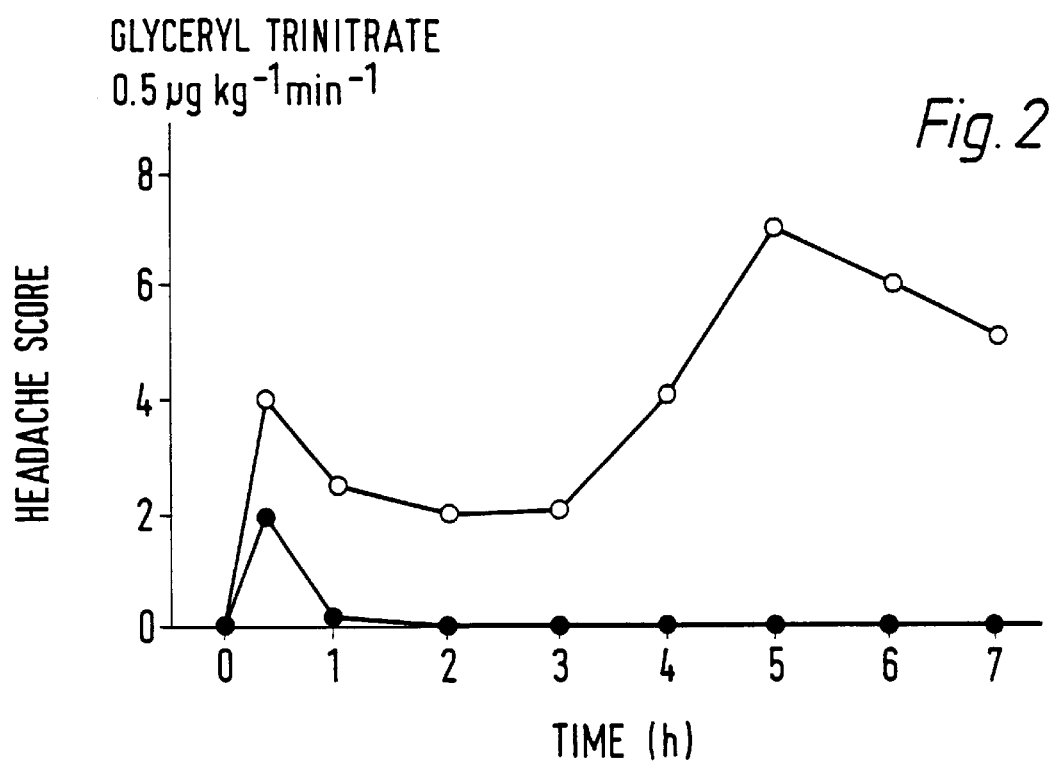
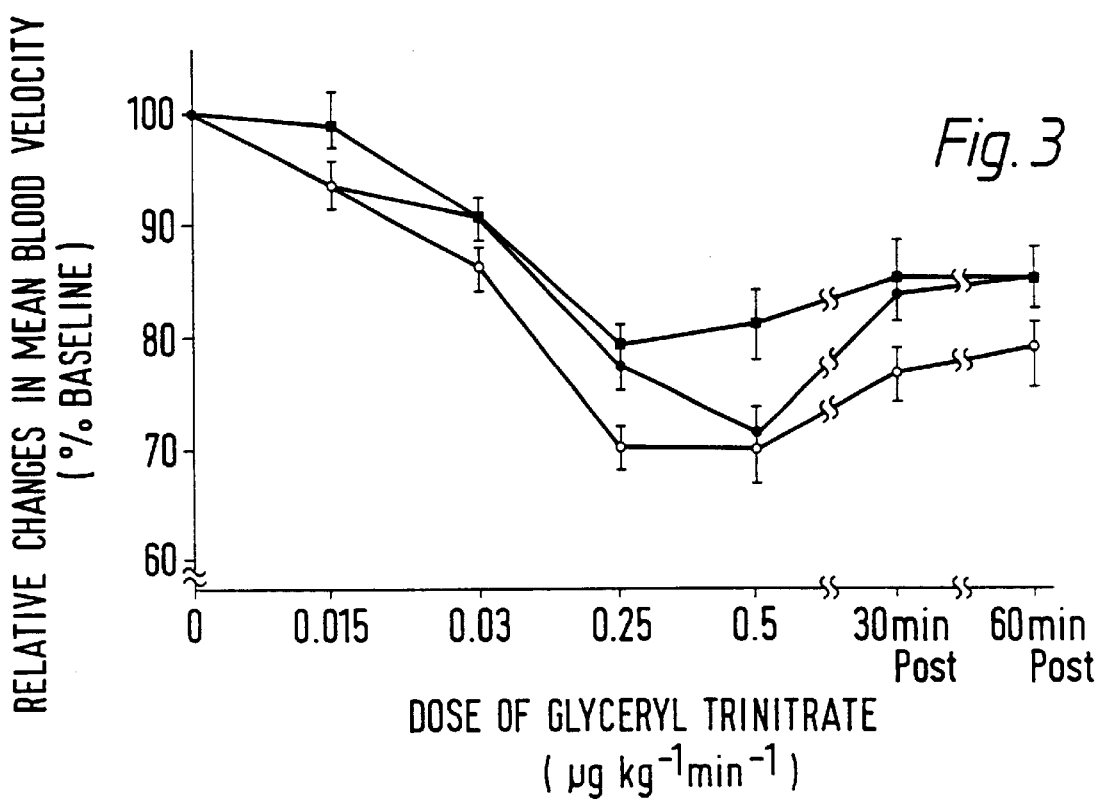

USE OF NO SCAVENGERS, INHIBITORS OF ANTAGONISTS IN THE TREATMENT OF MIGRAINE

The present invention relates to the use of a NO scavenger or an inhibitor or antagonist in the prophylactic or acute treatment of migraine or other vascular headaches in mammals including humans.

Many theories for the causation of migraine have been proposed and some have been reviewed.

It has been known for a century that nitroglycerin or glyceryl trinitrate may induce headache. Glyceryl trinitrate, which may be regarded as a prodrug for nitric oxide, induces a mild to moderate headache in healthy subjects. The present inventor and co-workers have previously made an investigation (Olesen et al., NeuroReport 4, 1027–1030 (1993)) to study whether migraine patients are more sensitive to nitric oxide than non-migrainous subjects, and it was found that glyceryl trinitrate-induced headache was significantly more severe in migraine sufferers, lasted longer and fulfilled diagnostic criteria for migraine more often. However, it has not hitherto been recognized that migraine as distinct fom headache in general is induced by glyceryl trinitrate and histamine, nor that they do so by activating the nitric oxide-cyclic guanylate monophosphate (cGMP) pathway and that this pathway could play a central role in the pathophysiology of migraine or other vascular headaches, as explained in more detail below.

The vascular pathophysiology of migraine has been evaluated in considerable detail. The migraine aura is throught to be caused by a cortical spreading depression (a slowly spreading depolarization of neurones and glial cells), and the pain is probably due to depolarization of perivascular nerve terminals cortically and/or around the large basal cerebral and extracerebral arteries. However, these findings do not explain the pain in migraine without aura. On the basis of animal experiments, it has been suggested that migraine pain is due to perivascular neurogenic inflammation around dural and meningeal arteries. This process is known to be associated with liberation of neuropeptide transmitters from perivascular trigeminal nerve endings.

During migraine attacks, concentrations of substance P (the primary mediator of neurogenic inflammation) remain normal in the external jugular venous blood whereas concentrations of calcitonin gene-related peptide (CGRP) are increased. However, substance P and CGRP are not likely to be the primary chemical mediators of migraine pain, since neither substance causes significant pain when injected into the temporal muscle and CGRP does not cause a headache when infused intravenously in humans. Although these substances could be nociceptive when released locally in high concentrations, it appears that other molecules may be more important.

Nitric Oxide and Pain

Nitric oxide (NO) has a large number of effects throughout the human body. It is a free radical which is highly reactive and is a molecular effector of activated-macrophage-induced cytotoxicity. Furthermore, it is the most important of the endothelium-derived relaxing factors. After its formation, NO diffuses into vascular smooth muscle where it activates soluble guanylate cyclase. This results in the formation of cGiW which, in turn, relaxes the muscle and dilates the blood vessels. Nitric oxide synthase catalyses the synthesis of NO from L-arginine, and this enzyme is present in nerve fibres surrounding cerebral blood vessels in animals and humans. However, the effect of nitric oxide formed in these nerves is unknown. Nitric oxide is also found in the CNS and has been shown to play an important role in the central processing of painful stimuli, it facilitates the transmission of noxious impulses from the periphery to the thalamus and the neocortex and, therefore, enhances pain.

The present inventor has now found that the nitric oxide-cyclic GNP pathway plays a central role in the pathophysiology of vascular headaches. In particular the present invention can be expressed in three parts as follows:

1. Activation of the nitric oxide-cyclic GMP pathway causes migraine in migraineurs cluster headache in cluster headache sufferers and non-specific vascular headache in others.
2. Drugs which are effective in the treatment of migraine and other vascular headaches and which are not general analgesics exert their activity by inhibiting one or more steps in the nitric oxide-cyclic GMP pathway or by exerting effects which antagonize the effects of products of this pathway.
3. Substances which cause vascular headache do so by stimulating one or more steps in the nitric oxide-cyclic GMP pathway or by exerting effects which are agonistic to those of one or more steps in this pathway.

More particularly the said investigations described below indicate that NO scavengers or inhibitors or antagonists can be used for the treatment of migraine or other vascular headaches.

Accordingly, the present invention provides the use of a NO scavenger or of an inhibitor or antagonist for an enzyme, coenyme, cofactor or other factor in, or product of, the nitric oxide-cyclic GMP pathway, for the production of a pharmaceutical composition for the prophylactic or acute treatment of migraine or other vascular headaches in mammals.

Suitably, the active principle used accordingly to the invention is a NO synthase inhibitor or a guanylate cyclase inhibitor. Furthermore, the active principle used according to the invention may suitably be a cGMP antagonist, an antagonist to a cGMP dependent protein kinase, or a NO scavenger.

Furthermore, the present invention provides a method for the prophylactic or acute treatment of migraine or other vascular headaches in mammals, which comprises administering to said mammal an effective amount for said treatment of a NO scavenger or of an inhibitor or antagonist for an enzyme, coenzyme, cofactor or other factor in, or product of, the nitric oxide-cyclic GMP pathway.

Suitably the NO synthase inhibitor used according to the invention is an arginine derivative such as those described in U.S. Pat. No. 5,028,627 and preferably it is L-NMMA, i.e. L-NG-monomethylarginine.

L-NMMA is available from Sigma Chemical Company Limited, Fancy Road, Poole, Dorset BH17 7NH, England.

In this connection it should be mentioned that the NO synthase inhibitor used according to the invention is intended for inhibition of one or more of the NO synthase enzymes known.

Suitably the guanylate cyclase inhibitor used according to the invention is methylene blue.

Suitable NO scavengers include transition metal complexes as described in International Patent Application W094/26263, for example Ferrioxamine B and Diethylenetriaminepentaacetic acid, Iron (III).

Many NO synthase inhibitors, for example L-NMMA, are capable of forming salts. Thus, the present invention includes NO synthase inhibitors in the form of salts, in particular acid addition salts.

Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of NO synthase inhibitors can be made by reacting the appropriate compound in the form af the free base with the appropriate acid.

Whilst it may be possible for the NO synthase inhibitors to be administered as the raw chemical, it is preferable to present them as a pharmaceutical formulation. According to a further aspect, the present invention provides a pharmaceutical formulation comprising the NO synthase inhibitor or a pharmaceutically acceptable salt or solvate thereof, together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association the NO-synthase inhibitor or a pharmaceutically acceptable salt or solvate thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspension which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for examples those suitable for oral administration may include flavouring agents.

The NO synthase inhibitors of the invention may be administered orally or via injection at a dose of from 1 to 100 mg/kg per day. When the NO synthase inhibitors are given by injection, this will normally be in the form of an intravenous bolus or by infusion, preferably the latter. The dose range for adult humans is generally from 70 mg to 2.5 g/dag and preferably 150 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

L-NMMA is preferably administered by injection, conveniently in the form of an infusion so that between 5 and 250 mg/kg of L-NMMA is administered per day. L-NMMA may also be administered by intravenous bolus in which case the maximum dose per bolus is 20 mg/kg and preferably 10 mg/kg, the total amount of L-NMMA administered by this method in a day will be between 5 og 250 mg/kg.

The dose of the NO synthase inhibitor will vary according to the potency of the inhibitor, its selectivity for the inducible form of the enzyme and the dose at which adverse pharmacological effetcs become evident. The man skilled in the art will take these factors into account when determining the dose of inhibitor to be administered.

What is stated above as to NO synthase inhibitors, formulations, doses and administration of said-inhibitors, applies also to the other active principles used according to the invention, as far as they are capable of forming salts, suitable for the formulations stated, effective in the doses stated, and suitable for the route of administration stated, respectively.

The present invention is based on extensive investigations carried out by the inventor and described in detail below.

In the following description of investigations carried out reference is made to the drawings comprising FIGS. 1 to 4. The legends belonging to said Figures are as follows.

FIG. 1. Mean headache scores (0–10 scale) during and after four doses of intravenous glyceryl trinitrate in normal headache-free subjects on day 2 of two separate study days. Glyceryl trinitrate was infused for ten minutes, and during this period a rapid increase in headache was observed. This was followed by a ten minute wash-out period, which resulted in a rapid decrease in headache. There was a relatively low day-to-day variation and a ceiling effect at approximately 0.5 µg kg−1 min−1.

FIG. 2. Comparison of the mean headache scores (0–10 scale) in response to glyceryl trinitrate (0.5 µg kg−1 min−1 for 20 min) in migraineurs (open circles) and non-migraineurs (closed circles).

FIG. 3. Relative changes in mean blood velocity ±SEM in the middle cerebral artery during four ascending doses of glyceryl trinitrate infusion in human controls (closed circles), tension-type headache sufferers (closed squares) and migraine sufferers (open circles).

Figure 4:
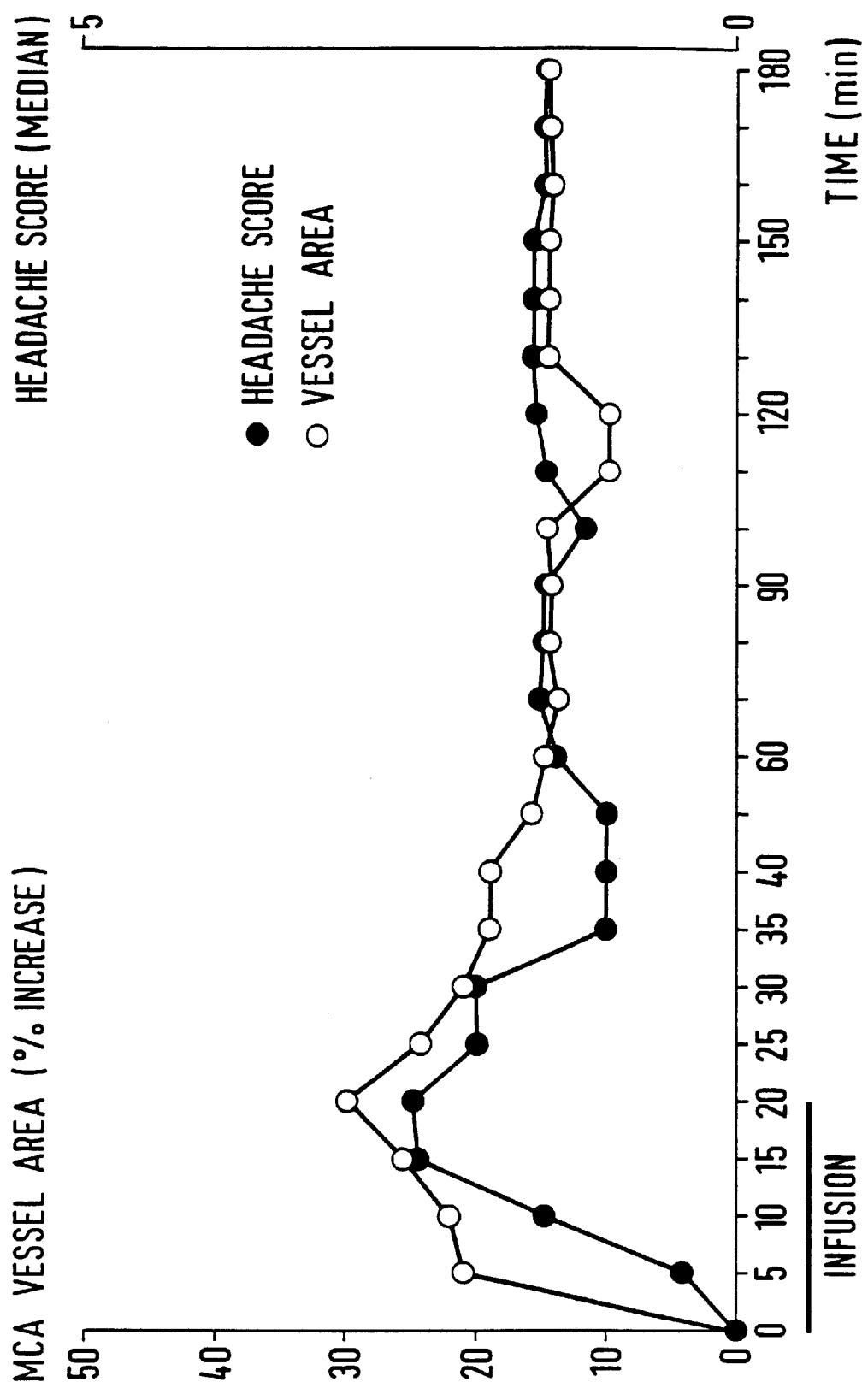

FIG. 4. Relation between headache intensity and middle cerebral artery (MCA) blood velocity response to nitroglycerin during the 3 hours where transcranial Doppler measurements were done. Headache score (median) and estimated changes in MCA vessel are shown for comparison.

Figure 5:
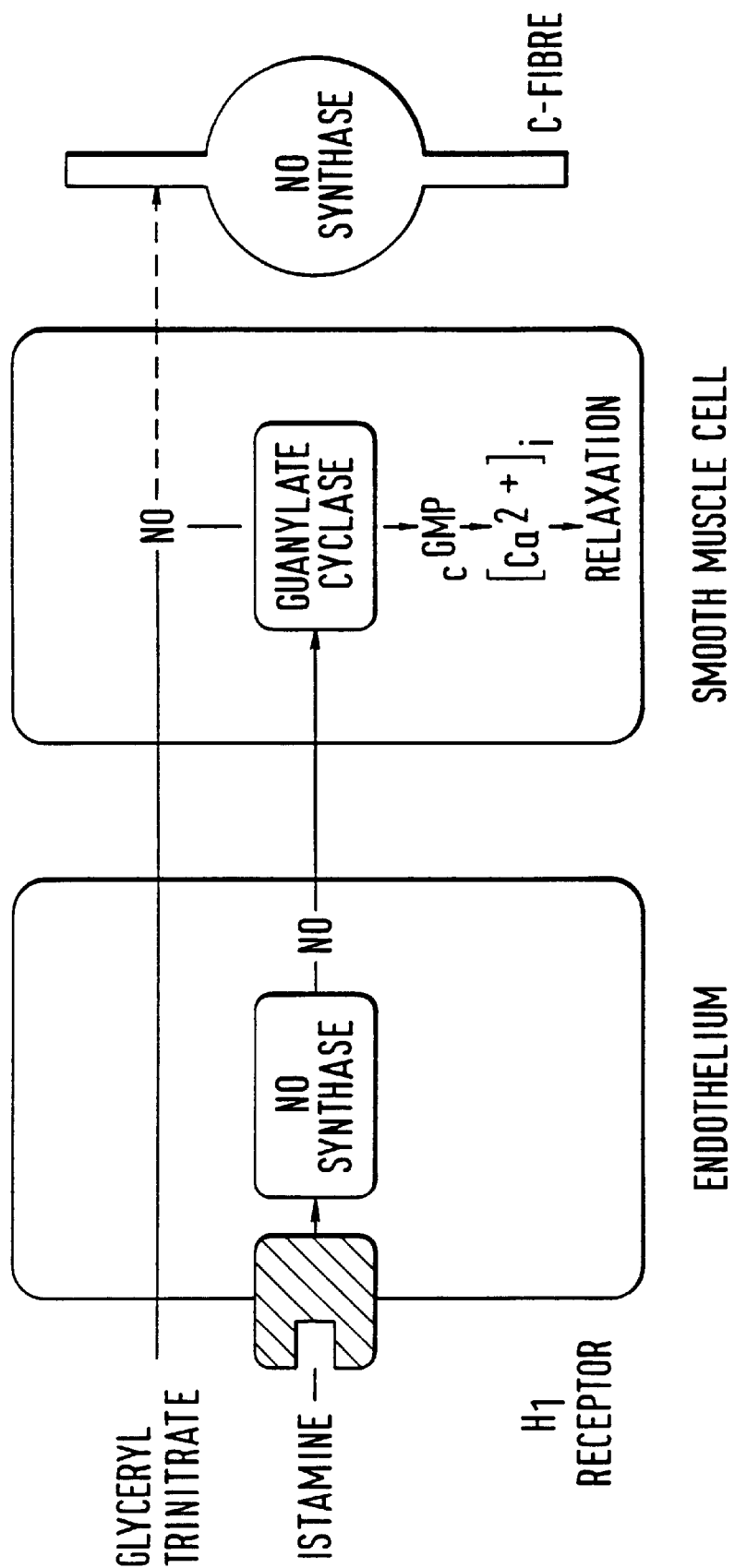

FIG. 5. Possible mechanisms of nitric oxide (NO)-induced headaches. Glyceryl trinitrate diffuses through cerebral arterial endothelium and in smooth muscle cells it is converted to NO by mechanisms that are independent of NO synthase. Histamine, by interaction with the histamine H1 receptor, activates NO synthase, which catalyses the formation of NO in the endothelium. Nitric oxide then diffuses into vascular smooth muscle. Nitric oxide from any source binds to the haeme moiety of guanylate cyclase and starts a chain of reactions that result in smooth muscle relaxation. It is unknown whether NO also reaches the perivascular nerves where, theoretically it might excite C-fibers that project to the trigeminal ganglion. [$Ca^{2+}$]I cytosolic $Ca^{2+}$ concentration.

Glyceryl trinitrate may as previously mentioned be regarded as a pro-drug for nitric oxide since its biological effects are due to the formation of NO. It is a lipid soluble molecule and hence easily crosses biological membranes, including the blood-brain barrier. Nitric oxide itself cannot be used experimentally because of its rapid inactivation, and therefore glyceryl trinitrate has been used to study experimental headache associated with NO (FIG. 1).

Continuous intravenous infusion of glyceryl trinitrate caused a dose-dependent and reproducible headache for the duration of the infusion, and the headache disappeared rapidly after discontinuation of the infusion. No pain was experienced in any other part of the body. In normal volunteers, the induced headache had some, but not all, of the characteristics of migraine attacks. A dose-dependent dilatation of the radial and superficial temporal arteries occurred in parallel with the headache, but headache tended to disappear faster than the vascular dilatation. Neither headache nor arterial dilatation increased when the dose of glyceryl trinitrate exceeded 0.5 µg kg−1 min−1 (ceiling effect). Both headache and arterial dilatation lasted several hours in response to isosorbide mononitrate, a long-acting nitrate. Headache was augmented by pretreatment with acetylcysteine, a donor of thiol groups, which is known to potentiate the effect of nitrates on the cardiac circulation. The potentiating effect on headache was paralleled by an increased dilatory response of the superficial temporal but not of the radial artery.

In an attempt to evaluate whether headache induced by glyceryl trinitrate was secondary to histamine release, normal volunteers were pretreated double blindly with mepyramine (a histamine H1 receptor antagonist) or saline prior to infusion of glyceryl trinitrate. Previous studies have shown that mepyramine almost completely blocks histamine-induced headache but there was no effect of mepyramine on glyceryl-trinitrate-induced headache and, therefore, this was not secondary to histamine release. Glyceryl trinitrate dilated large cerebral arteries but did not cause any change in cerebral blood flow, indicating that it has no effect on cerebral arterioles. These changes were similar to those reported by some authors during attacks of migraine without aura where large cephalic arteries may have been dilated but cerebral blood flow remained normal.

Evidence has suggested for many years that migraineurs are more sensitive to glyceryl trinitrate than non-migraineurs. These studies, however, adhered only partly to present-day requirements of double-blind controlled experimental conditions. The characteristics used to define migraine headache were not prospectively scored and dose response relationships were not explored.

In a recent study, 17 migraineurs were compared with 17 headache-free control subjects and with a group of tension-type headache sufferers. Glyceryl trinitrate was given as continuous intravenous infusion in four ascending doses. The total amount of headache (sum of pain scores) during the experimental period was significantly greater in migraineurs than in tension-type headache sufferers or headache-free controls (FIG. 2). Headache in migraineurs more often fulfilled the operational diagnostic criteria for migraine of the International Headache Society (Head-ache Classification Committee of the International Headache Society (1988) Cephalalgia 8 (Suppl. 7), 1–96) and was significantly more intense than in normal subjects. After the infusion, headache rapidly diminished or disappeared in non-migraineurs, but it was only moderately reduced 60 min after infusion in migraineurs. None of the control subjects but 14 out of 17 migraineurs required specific migraine treatment after the infusion. Within 24 h after the infusion, 11 of the 17 migraineurs developed a headache that they characterized as a typical migraine. Furthermore, the increased sensitivity to glyceryl trinitrate in migraineurs was not just subjective since transcranial Doppler measurements showed that blood velocity in the middle cerebral artery was significantly more reduced during glyceryl trinitrate infusion in migraineurs than in non-migraineurs (FIG. 3). Regional cerebral blood flow was unchanged by glyceryl trinitrate, and hence this indicated that glyceryl trinitrate caused increased dilatation of the middle cerebral artery in migraine sufferers.

In a further study to examine whether the nitric oxide donor nitroglycerin induces a typical migraine attack, to exclude placebo related effects and to describe the relation between middle cerebral artery dilatation and provoked migraine, each patient randomly received an intravenous infusion of nitroglycerin (0.5 µg/kg/min) or saline for 20 minutes on two different study days at least 7 days apart. On both days headache was scored on a 10 point vertical scale: 1 representing a very rild headache (includingfeeling of pressing or throbbing), 5 a moderate headache and 10 the worst possible headache. Furthermore, headache characteristics were repeatedly recorded and compared with the diagnostic criteria of the International Headache Society (IHS). Of the patients completing the study, 8 out of 10 fulfilled the diagnostic criteria of the IHS for migraine without aura. Furthermore, all patients who normally had unilateral spontaneous migraine attacks also had unilateral headaches after nitroglycerin. Only one subject developed migraine after placebo which rulwa out a placebo response as the cause of nitric oxide (nitroglycerin)-induced migraine. The time pattern of headache and estimated middle cerabral artery dilatation correspond well (FIG. 4). Table 1 indicates the clinical characteristics of: (a) spontaneous migraine attacks, (b) headache during nitroglycerin infusion (20 min) and (c) peak headache post-nitroglycerin infusion.

TABLE 1

| Subject | Time (hours) | Headache (localisation/Intensity/quality) | Aggravated | Accompanying symptoms (vomit/nausea/photo./phono.) (% of usual attacks) | Migr. |
|---|---|---|---|---|---|
| 1 a |   | Right/severe/throb | yes | 50%/100%/100%/100% | yes |
| b |   | Right/7/throb |   | No/yes/yes/no | yes |
| c | 3 | Right/10/throb | yes | No/yes/yes/yes | yes |
| 2 a |   | Right of left/severe/throb | no | 1%/20%/100%/100% | yes |
| b |   | Bilat/3/throb |   | No/no/no/no | no |
| c | 3 | Left/8/throb | yes | No/yes/yes/yes | yes |
| 3 a |   | Right or left/severe/pres. | yes | 100%/100%/0%/0% | yes |
| b |   | No headache |   |   |   |
| c | 10 | Left/9/pres | yes | No/yes/yes/yes | yes |
| 4 a |   | Bilat/severe/throb | yes | 100%/100%/100%/100% | yes |
| b |   | Bilat/3/pres |   | No/no/no/no | no |
| c | 3 | Bilat/1/throb | no | No/no/no/no | no |
| 5 a |   | Bilat/severe/throb | yes | 0%/100%/100%/100% | yes |
| b |   | Bilat/2/throb |   | No/no/no/no | no |
| c | 8 | Bilat/8/throb | yes | No/yes/yes/yes | yes |
| 6 a |   | Left/severe/throb | yes | 100%/100%/100%/100% | yes |
| b |   | Left/5/throb |   | No/no/yes/no | no |
| c | 6 | Left/3/pres | yes | No/no/yes/yes | yes |
| 7 a |   | Bilat/severe/throb | yes | 0%/100%/100%/100% | yes |
| b |   | Bilat/2/pres |   | No/no/no/no | no |
| c | 8 | Bilat/5/pres | yes | No/yes/no/no | yes |
| 8 a |   | Bilat/moderate/throb | yes | 0%/100%/100%/100% | yes |
| b |   | Bilat/1/throb |   | No/no/no/yes | no |
| c |   | No headache |   |   |   |
| 9 a |   | Left or Bilat/moderate/throb | yes | 0%/0%/100%/100% | yes |
| b |   | Right/3/throb |   | No/no/yes/no | no |
| c | 5 | Right/6/throb | yes | No/yes/yes/no | yes |
| 10 a |   | Bilat/moderate/throb | yes | 50%/100%/100%/100% | yes |
| b |   | No headache |   |   |   |
| c | 7 | Bilat/3/throb | yes | No/yes/yes/yes | yes |

(bilat., bilateral; throb., throbbing; pres., pressing; photo., photophobia; phono., phonophobia; migr., fulfilling the IHS criteria for migraine without aura; aggravated, headache aggravation by physical activity; time, time to post-infusion peak in hours.)

Involvement of Endosenous NO in Migraine Attacks

In a controlled trial, migraine sufferers developed a medium to severe pulsating headache during histamine infusion whereas control subjects did not develop such a headache. The effect was blocked almost completely by mepyramine, and a small effect of cimetidine (a H2 receptor antagonist) was also observed. Recent studies of the effect of histamine on cranial arteries in primates and humans strongly suggested that histamine causes dilatation by activating an endothelial H1 receptor and thereby induces the formation of NO. Therefore histamine-induced headache is most likely to be a consequence of the formation of NO in cranial blood vessels.

Prosstacyclin is another substance with a potential to cause headache. It has different effects in different vascular beds and in different species, and its effect in human cranial blood vessels have not been fully elucidated. However, in some species and in some vascular beds prostacyclin induces the formation of NO. In addition, glyceryl trinitrate applied locally to the pial surface induces release of CGRP from perivascular nerve fibres, and hence the observed increase in concentrations of CGRP during migraine attacks may be secondary to NO formation.

Involvement of NO in Additional Types of Headache.

Cluster Headache Attacks

Administration of glyceryl trinitrate to patients with cluster headache during a cluster period (usually patients have only 1–2 attacks a day lasting 30 min) resulted in the development of a typical cluster headache attack in all the patients with a latency of 30–50 minutes. Subsequent studies confirmed the provocation of typical cluster headache attacks by glyceryl trinitrate. Histamine, via induction of cerebro-vascular endogenous NO formation as discussed above, may also cause cluster headache attacks in sufferers. As for migraine, NO triggers attacks only in susceptible individuals and after a surprisingly long latency period. Therefore, in both conditions it appears that NO initiates a slow pathological reaction that, eventually, leads to the attack.

Syymptomatic Vascular Headaches

Meningitis and encephalitis, which cause servere headache, result in the formation of cytokines that stimulate macrophage production of NO. Endotoxin stimulates the formation of cytokines and it has been shown recently that migraineurs are more sensitive to endotoxin than non-migraineurs.

Hypoxia is another known cause of vascular headache and pure oxygen has been used as an effective treatment for cluster headache. Hypoxia increases the concentration of NO in blood vessels from several species whereas hyperoxia enchances the inactivation of NO and thereby shortens and diminishes its effect.

Following trauma, headache often occurs with a delay of hours or days. An inflammatory reaction develops after a similar time delay, and this is known to cause an increased formation of NO via the induction of NO synthase. Thus, the vascular component of posttraumatic headache could be caused by endogenous formation of NO. Ischaemic cerebrovascular disease is quite often associated with headache of a vascular type, and in approximately ten per cent of cases, headache occurs before the stroke (this is known as a sentinel headache). During platelet aggregation and thrombus formation, a number of substances such as 5-hydroxytryptamine, platelet-activating factor, thrombin and prostacyclin are released, and several of these stimulate the formation of NO in cerebral vascular endothelium. Therefore, both sentinel headache and headache during stroke could be secondary to thrombus formation and increased vascular concentrations of NO.

The formation of NO in a cerebral artery is shown in FIG. 5. A possible mechanism whereby NO could cause headache is by dilatation of cerebral and extracerebral blood vessels, and this is supported by studies in which arterial dilatation during and after infusion of glyceryl trinitrate was consistently observed. However, this may not be the only or even the most important mechanism since in healthy subjects the dilatation persists longer than the headache. Furthermore, moderate mechanical dilatation may not cause pain even though vigorous dilatation in association with balloon angioplasty does induce severe headache. Another possibility is that NO causes headache via a direct effect on perivascular sensory nerves. Nitric oxide synthase is present in cerebral periarterial nerves, and predominantly in those arising from the sphenopalatine ganglion. Few if any of the fibers projecting to the trigeminal ganglion contain NO synthase. However, cerebral neurones that do not contain NO synthase are particularly vulnerable to the toxic effects of NO, and since NO is a noxious molecule, it might activate sensory nerve fibres directly.

It is not yet understood why migraine sufferers respond with more intense headache to NO than healthy controls. The increased sensitivity is seen in response to both glyceryl trinitrate (which is independent of NO synthase) and to histamine (which is dependent on NO synthase (FIG. 5)). Thus, increased activity of NO synthase cannot explain the findings observed with glyceryl trinitrate, and decreased activity of NO synthase with secondary upregulation of guanylate cyclase cannot explain the findings observed with histamine. Increased conversion of glyceryl trinitrate to NO in migraineurs could explain the increase sensitivity to glyceryl trinitrate but not to histamine. Therefore, it can be concluded that the disturbance in migraineurs must be downstream from NO, for example, an increase of the activity of guanylate cyclase or another enzyme and/or cofactor and/or receptor in the NO-triggered cascade of reactions. Alternatively, migraine patients may be more vulnerable to one of the many toxic effects of NO such as enzyme inhibition and formation of peroxynitrate with lipid peroxydation.

What is claimed is:

1. A method for prophylactic or acute treatment of migraine or other vascular headaches in a mammal suffering from migraine or other vascular headaches or in a mammal having the history of migraine or other vascular headaches, which comprises administering to said mammal an effective amount for said treatment of an active principle which is a NO synthase inhibitor or a salt thereof;

with the proviso that, when said NO synthase inhibitor or salt thereof is an arginine analogue of the formula

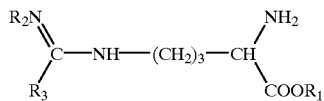

wherein $R_1$ represents a hydrogen atom or a methyl or ethyl group, $R_2$ represents a hydrogen atom or a nitro group and $R_3$ represents an amino, methylamino, ethylamino, hydrazino, methyl or ethyl group, then it is not in the form of a salt or amide of a cyclooxygenase inhibitor.

2. A method according to claim 1 wherein the NO synthase inhibitor is L-NMMA.

3. A method according to claim 1 wherein the active principle is an acid addition salt of said synthase inhibitor.

4. A method according to claim 1 wherein the NO synthase inhibitor is administered orally or by injection at a dose of from 1 to 100 mg/kg per day.

5. The method of claim 1 which is limited to the acute treatment of migraine or other vascular headache in a mammal wherein said active principle is administered to a mammal suffering from said migraine or other vascular headache.

6. The method of claim 5 wherein the NO synthase inhibitor is L-NMMA.

7. The method of claim 5 wherein the active principle is an acid addition salt of a synthase inhibitor.

8. The method of claim 5 wherein the NO synthase inhibitor is administered orally or by injection at a dose of from 1 to 100 mg/kg per day.

9. A method for treating cluster headache in a mammal, which comprises administering to said mammal an effective amount for said treatment of an active principle which is a NO sythase inhibitor or salt thereof with the proviso that, when said NO synthase inhibitor or salt thereof is an arginine analogue of the formula

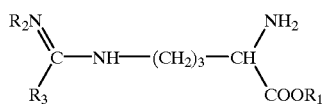

wherein $R_1$ represents a hydrogen atom or a methyl or ethyl group, $R_2$ represents a hydrogen atom or a nitro group and $R_3$ represents an amino, methylamino, ethylamino, hydrazino, methyl or ethyl group, then it is not in the form of a salt or amide of a cyclooxygenase inhibitor.

* * * * *